US009788837B2

United States Patent
Ahonen et al.

(10) Patent No.: US 9,788,837 B2
(45) Date of Patent: *Oct. 17, 2017

(54) METHODS, COMPOSITIONS AND KITS FOR PERFORMING ANASTOMOSIS PROCEDURES IN CONJUNCTION WITH A RADICAL PROSTATECTOMY PROCEDURE

(71) Applicant: Boston Scientific Scimed, Inc., Maple Grove, MN (US)

(72) Inventors: David A Ahonen, Wellesley, MA (US); Wendy Bosworth, Atlanta, GA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/715,107

(22) Filed: May 18, 2015

(65) Prior Publication Data

US 2015/0257761 A1    Sep. 17, 2015

Related U.S. Application Data

(63) Continuation of application No. 13/570,635, filed on Aug. 9, 2012, now Pat. No. 9,060,749.

(Continued)

(51) Int. Cl.
*A61B 17/11* (2006.01)
*A61B 17/00* (2006.01)
(Continued)

(52) U.S. Cl.
CPC .............. *A61B 17/11* (2013.01); *A61B 17/00* (2013.01); *A61B 17/12045* (2013.01);
(Continued)

(58) Field of Classification Search
CPC ... A61B 17/11; A61B 17/00; A61B 17/12045; A61B 2017/1132; A61B 17/12181;
(Continued)

(56) References Cited

U.S. PATENT DOCUMENTS 4,873,977 A    10/1989 Avant et al.
5,047,039 A    9/1991 Avant et al.
(Continued)

OTHER PUBLICATIONS

H.B. Nirmal et al., International Journal of PharmTech Research, vol. 2, No. 2, pp. 1398-1408, Apr.-Jun. 2010.

*Primary Examiner* — Katherine M Shi
*Assistant Examiner* — Michael Mendoza
(74) *Attorney, Agent, or Firm* — Bookoff McAndrews, PLLC (57) ABSTRACT

In some aspects, a surgical procedure for the removal of a prostate gland is provided. The procedure comprises: (a) positioning an implant material within the urethra, (b) removing the prostate, thereby cresting a urethral stump and a bladder neck, wherein the implant material occupies the urethral stump, the bladder neck, or both, and (c) securing the bladder neck to the urethral stump in an anastomosis procedure to establish a path of urine flow from the bladder to an external urethral opening (e.g., the meatus). Subsequently, the implant material is removed from the urethra, for example, by natural urine voiding or by flowing a removal fluid through and/or around the implant material in the urethra. In other aspects, a medical kit is provided.

20 Claims, 4 Drawing Sheets

Related U.S. Application Data (60) Provisional application No. 61/523,030, filed on Aug. 12, 2011.

(51) Int. Cl.
*A61B 17/12* (2006.01)
*A61F 2/04* (2013.01)
*A61F 2/86* (2013.01)
*A61B 18/00* (2006.01)

(52) U.S. Cl.
CPC .................. *A61F 2/04* (2013.01); *A61F 2/86* (2013.01); *A61B 17/00491* (2013.01); *A61B 17/12159* (2013.01); *A61B 17/12181* (2013.01); *A61B 17/12195* (2013.01); *A61B 2017/00274* (2013.01); *A61B 2017/1132* (2013.01); *A61B 2018/00505* (2013.01); *A61B 2018/00517* (2013.01); *A61F 2002/041* (2013.01); *A61F 2210/0014* (2013.01)

(58) Field of Classification Search
CPC   A61B 2018/00517; A61B 2018/00505; A61B 17/12195; A61B 2017/00274; A61B 17/12159; A61F 2/04; A61F 2/86; A61F 2002/041; A61F 2210/0014
See application file for complete search history.

(56) References Cited

U.S. PATENT DOCUMENTS

| | | |
|---|---|---|
| 5,591,179 A | 1/1997 | Edelstein |
| 6,152,943 A | 11/2000 | Sawhney |
| 7,510,560 B2 | 3/2009 | Manzo |
| 7,666,197 B2 | 2/2010 | Orban, III |
| 2005/0165426 A1 | 7/2005 | Manzo |
| 2005/0171563 A1 | 8/2005 | Heinrich et al. |
| 2008/0181952 A1 | 7/2008 | Vogel et al. |
| 2008/0208163 A1 | 8/2008 | Wilkie |
| 2008/0262519 A1 | 10/2008 | Gurtner et al. |

METHODS, COMPOSITIONS AND KITS FOR PERFORMING ANASTOMOSIS PROCEDURES IN CONJUNCTION WITH A RADICAL PROSTATECTOMY PROCEDURE

CROSS REFERENCE TO RELATED APPLICATIONS

This application is a continuation of U.S. Ser. No. 13/570,635, filed Aug. 9, 2012 and entitled "METHODS, COMPOSITIONS AND KITS FOR PERFORMING ANASTOMOSIS PROCEDURES IN CONJUNCTION WITH A RADICAL PROSTATECTOMY PROCEDURE," which claims the benefit of U.S. Ser. No. 61/523,030, filed Aug. 12, 2011 and entitled "METHODS, COMPOSITIONS AND KITS FOR PERFORMING ANASTOMOSIS PROCEDURES IN CONJUNCTION WITH A RADICAL PROSTATECTOMY PROCEDURE," each of which is hereby incorporated by reference in its entirety.

FIELD OF THE INVENTION

The present invention relates, among other things, to methods, compositions and kits for performing an anastomosis in conjunction with radical prostatectomy procedure.

BACKGROUND OF THE INVENTION

Many body conduits are generally cylindrical in configuration and have a generally circular cross-section. The surgical attachment of one body conduit to another is commonly referred to as an anastomosis. The complexity of anastomosis attachment is made apparent in a surgical procedure referred to generally as a radical prostatectomy, which is a well-established surgical procedure, typically for patients with localized prostatic carcinoma.

In a radical prostatectomy, the surgeon removes all or most of the patient's prostate. Because the urethra travels through the prostate immediately before reaching the bladder, a portion of the upper part of the urethra is removed in the surgery. In order to restore proper urinary functions, the bladder neck and the urethral stump must be reconnected.

Typically, radical prostatectomy procedures require the removal of cancerous tissue while preserving sexual function and continence in the patient. There are two common types of radical prostatectomy approaches for the removal of prostate cancer, the retropubic approach and the perineal approach. In either procedure, the removal of the prostate gland results in the creation of a bladder neck and urethral stump which are attached together in an anastomosis procedure. Typically, the urethral opening at the end of the bladder neck is closed sufficiently (e.g., by stitching) so that its size approximates the size of the urethral opening at the end of the urethral stump. The bladder neck is then positioned against the urethral stump and the two are stitched together to create a new, shortened conduit (urethra) extending from the bladder to the external urethral opening (i.e., the urethral exit at the end of the penis, or meatus).

In each of the above described procedures, it is the attachment of the urethral stump to the bladder neck which is particularly difficult and complex. This difficulty is complicated by the tendency of the urethral stump to retract into adjacent tissue. As a result, considerable time and effort can be expended to re-expose the urethral stump and begin the re-anastomosis procedure. Further complicating this procedure is the fact that the urethral stump is positioned beneath the pubic bone thus requiring that the surgeon work at a difficult angle and in positions that are uncomfortable and limiting.

SUMMARY OF THE INVENTION

In some aspects, a surgical procedure for the removal of a prostate gland is provided. The procedure comprises: (a) positioning an implant material within the urethra, (b) removing the prostate, thereby creating a urethral stump and a bladder neck, wherein the implant material occupies the urethral stump, the bladder neck, or both, and (c) securing the bladder neck to the urethral stump in an anastomosis procedure to establish a path of urine flow from the bladder to an external urethral opening (e.g., the meatus). Subsequently, the implant material is removed from the urethra, for example, by natural urine voiding or by flowing a removal fluid through and/or around the implant material in the urethra.

In other aspects, a medical kit is provided. The medical kit comprising any combination of two or more of the following items: (a) an implant-forming composition or a pre-formed implant material, (b) an apparatus for establishing the pre-formed implant or implant-forming composition into the urinary tract (e.g., the prostate section of the urinary tract) of a subject, (c) a removal fluid, (d) a pump for pumping removal fluid into the urinary tract, (e) suitable packaging material and (f) printed material with one or more of the following: (i) storage information, (ii) instructions regarding how to administer the pre-formed implant material or implant-forming composition to the subject and (iii) instructions regarding how to administer the removal fluid to the subject.

These and other aspects, embodiments and advantages of the present disclosure will become immediately apparent to those of ordinary skill in the art upon review of the Detailed Description and any claims to follow

DETAILED DESCRIPTION

A more complete understanding of the present invention is available by reference to the following detailed description of numerous aspects and embodiments of the invention. The detailed description of the invention which follows is intended to illustrate but not limit the invention.

As used herein, the term "lumen" denotes the space enclosed by a tube-like structure, such as a catheter, or a hollow body organ, such as inside an artery, a vein, a kidney, a ureter, a urinary bladder, a urethra, a gall bladder, a pancreas, a salivary gland, a small intestine or a large intestine, among others.

As used herein, "subjects" are vertebrate subjects, more typically mammalian subjects, including human subjects, pets and livestock.

As used herein a "solid" material is one that, unlike a liquid, does not flow to take on the shape of its container (nor does it expand to fill the entire volume available to it like a gas does). As used herein, "solidification" is a process whereby a material either becomes a solid material or whereby liquid material undergoes an increase in viscosity (and thus more closely resembles a solid material).

In accordance with one embodiment, a surgical method is provided in which an implant material is inserted, injected, formed or otherwise established in the urethra such that the implant material is present at least within the urethral outlet (i.e., the portion of the urethra that lies on the downstream side of the prostate). The prostate is removed (e.g., resected), thereby creating a urethral stump (corresponding to the outlet portion of the urethra) which contains the implant material. The presence of the implant material in the urethral stump improves handling of the urethral stump (e.g., by minimizing retraction of the urethral stump, by stiffening the urethral stump, etc.). The bladder neck and urethral stump may then be grasped and drawn into contact with one another, and the bladder neck secured to the urethral stump in an anastomosis procedure. Upon removal of the implant material (e.g., by natural urine voiding, by flowing a removal fluid through and/or around the implant material in the urethra, etc.), a path of urine flow from the bladder to the external urethral opening (i.e., the urethral exit at the end of the penis, or meatus) is reestablished.

In certain embodiments, the implant material is inserted, injected, formed or otherwise established in the urethra such that (a) the implant material is present within the urethral outlet on the downstream side of the prostate and (b) the implant material is present within the bladder neck on the upstream side of the prostate. The prostate is removing, thereby creating a urethral stump which contains the implant material and a bladder neck which also contains the implant material. As above, the presence of the implant material in the urethral stump improves handling of the urethral stump (e.g., by minimizing retraction of the urethral stump, by stiffening the urethral stump, etc.). Similarly, the presence of the implant material in the bladder neck also improves handling of the same. The bladder neck and urethral stump may then be grasped and drawn into contact with one another, and the bladder neck is secured to the urethral stump in an anastomosis procedure. Upon removal of the implant material, a path of urine flow from the bladder to the external urethral opening is reestablished.

In certain of these embodiments, prior to removing the prostate, distinct regions of the implant material are established in the urethral outlet and bladder neck, respectively.

In certain other of these embodiments, prior to removing the prostate, a single implant material extends from the urethral outlet, through the prostatic urethra (i.e., the portion of the urethra that passes through the prostate) and into the bladder neck. Upon removal of the prostate, the implant material is severed, establishing distinct regions of the implant material in the urethral outlet (i.e., the material in the urethral stump) and bladder neck, respectively.

In certain embodiments, the process of drawing the bladder neck to the urethral stump is magnetically assisted, for example, by using an implant material which is magnetic (e.g., an implant material containing magnetised materials) or which is susceptible to a magnetic field (e.g., an implant material containing paramagnetic and/or ferromagnetic materials).

Where a paramagnetic and/or ferromagnetic material is employed, a magnetic field may be applied to the implant materials. By applying a magnetic field of suitable magnitude and direction, the implant materials (e.g., implant material within the urethral stump and implant material within the bladder neck) will be magnetically drawn toward one another.

Figure 1:
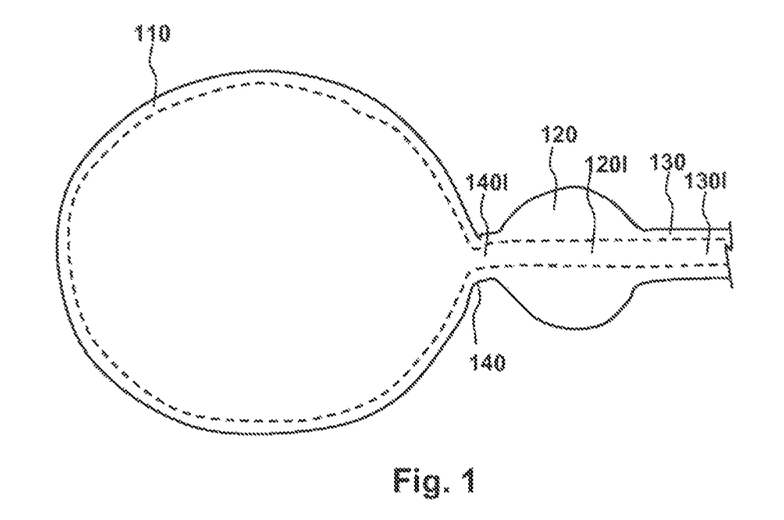
FIG. 1 is a schematic illustration of a portion of the urinary tract of a male subject.

Turning now to the drawings, in FIG. 1 there is shown a schematic illustration of a portion of the urinary tract of a male subject, which includes a bladder 110, bladder neck 140, prostate 120, and the urethral outlet 130. The bladder neck 140 is the area at the base of the bladder where the urethral lumen passes through the thickened musculature of the bladder base (referred to herein as the "bladder neck lumen" 1401). The prostatic urethra passes through the prostate gland 120. The prostatic urethral lumen is designated 1201 in FIG. 1. Also shown is the urethral outlet 130. The urethral outlet lumen is designated 1301 in FIG. 1.

Figure 2:
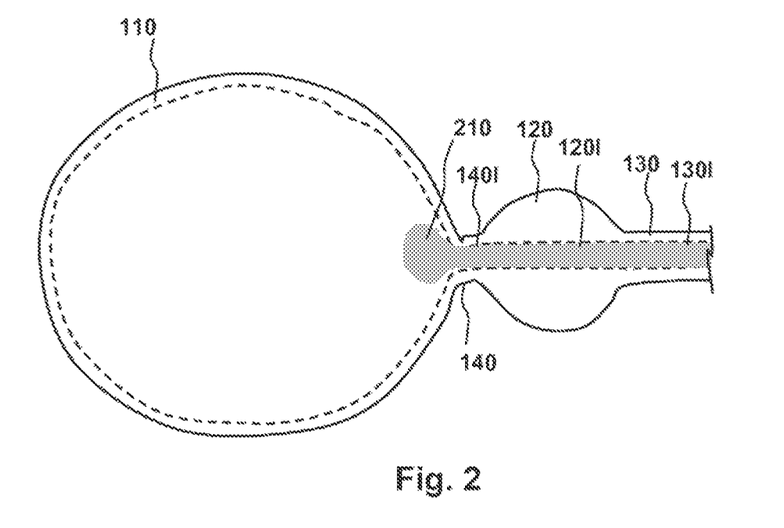
FIG. 2 is schematic illustration of a portion of the urinary tract of a male subject, after establishing an implant material within the bladder neck, prostatic urethra and the urethral outlet, in accordance with an embodiment of the invention.

In accordance with an embodiment of the present disclosure, prior to surgical removal of the prostate 120, an implant material 210 is inserted into the urethra such that it occupies the bladder neck lumen 1401, prostatic urethral lumen 1201 and urethral outlet lumen 1301 as shown in FIG. 2.

Figure 3:
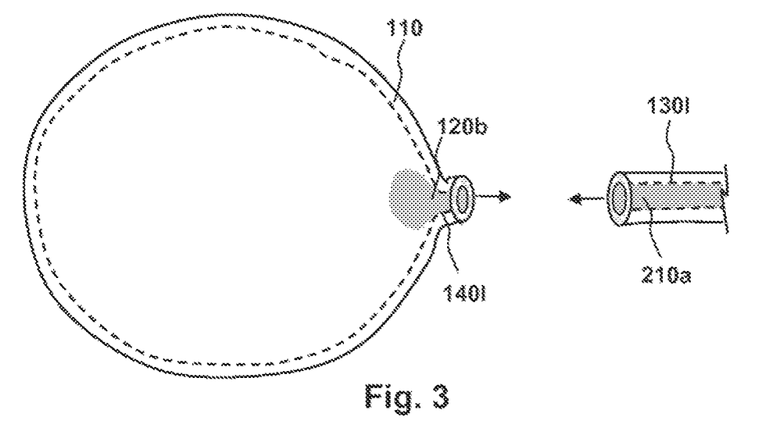
FIG. 3 is a schematic illustration of a portion of the urinary tract of a male subject as shown in FIG. 2, after removal of the prostate gland and a portion of the implant, in accordance with an embodiment of the invention.

Referring now to FIG. 3, the prostate gland is then surgically removed, resulting in a first region of implant material 120a being present in the urethral outlet lumen 1301 and a second region of implant material 120b being present in the bladder neck lumen 1401.

Figure 4:
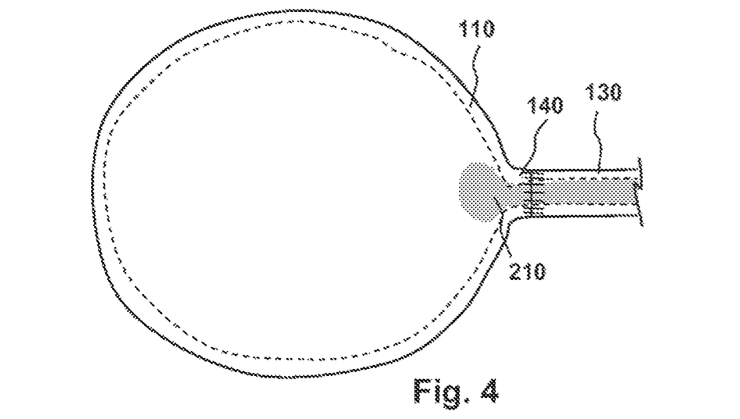
FIG. 4 is a schematic illustration of a portion of the urinary tract of a male subject as shown in FIG. 3, after the bladder neck is secured to the urethral stump in an anastomosis procedure, in accordance with an embodiment of the invention.

The bladder neck 140 and urethral stump of the urethral outlet 130 are then drawn into contact with one another, and the bladder neck 140 secured to the urethral stump of the urethral outlet 130 in an anastomosis procedure as shown in FIG. 4. For example, the bladder neck 140 may be secured to the urethral stump of the urethral outlet 130 by suturing, by use of a suitable surgical adhesive, or another suitable method.

Figure 5:
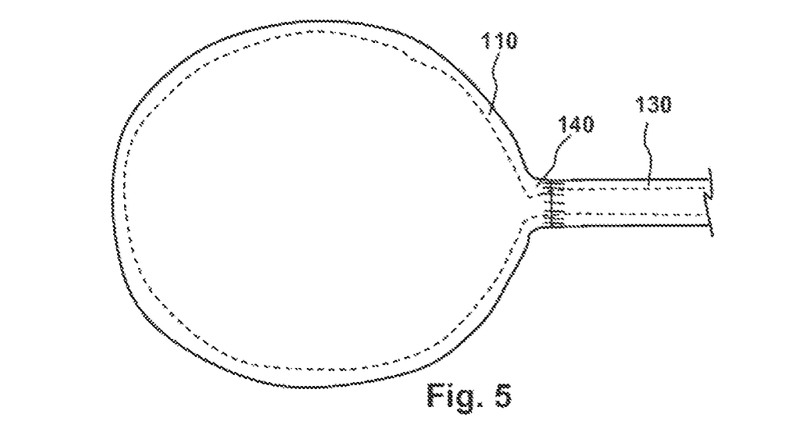
FIG. 5 is a schematic illustration of a portion of the urinary tract of a male subject as shown in FIG. 4, after removal of the implant material, in accordance with an embodiment of the invention.

Finally, the first and second regions of implant material 120a, 120b are removed, thereby reestablishing a path of urine flow from the bladder as shown in FIG. 5. The first and second regions of implant material 120a, 120b may be removed by natural urine flow or by using a suitable removal fluid as discussed below.

Figure 8:
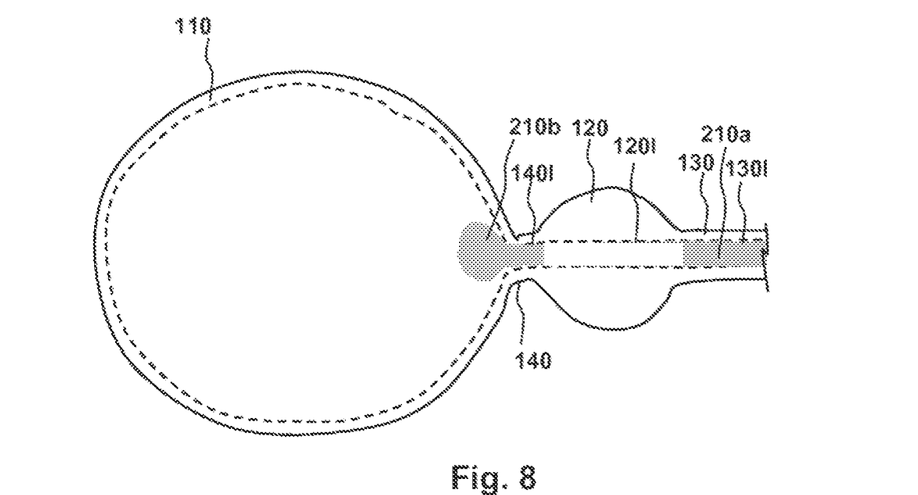
FIG. 8 is schematic illustration of a portion of the urinary tract of a male subject, after establishing an implant material within the bladder neck and the urethral outlet, in accordance with an embodiment of the invention.
Figure 9:
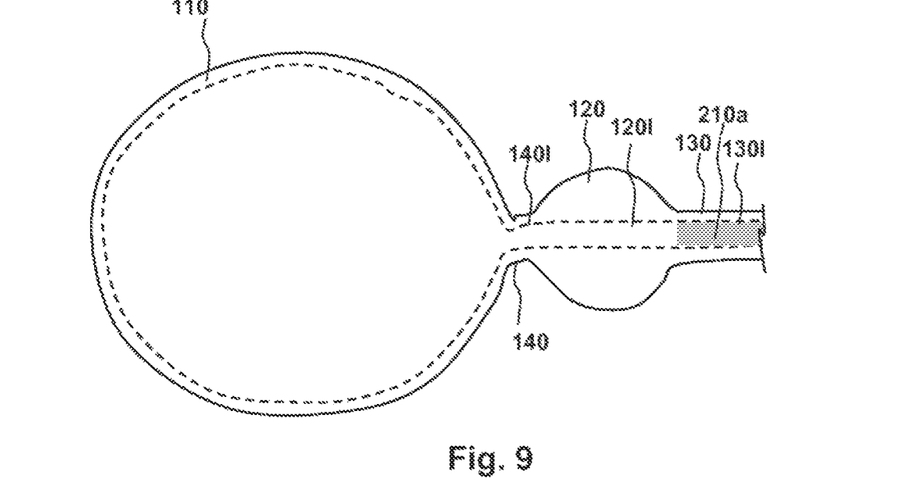
FIG. 9 is schematic illustration of a portion of the urinary tract of a male subject, after establishing an implant material within the urethral outlet, in accordance with an embodiment of the invention.

In accordance with another embodiment of the present disclosure, in an alternative to FIG. 2, a first region of implant material 120a is inserted into the urethra such that it occupies the bladder neck lumen 1401 and a distinct second region of implant material 120b is inserted into the urethral outlet lumen 1301 as shown in FIG. 8. In accordance with yet another embodiment of the present disclosure, in another alternative to FIG. 2, a first region of implant material 120a is inserted into the urethra such that it occupies the urethral outlet lumen 1301 as shown in FIG. 9. In either case, the prostate gland 120 is surgically removed, the bladder neck 140 is secured to the urethral stump of the urethral outlet 130 in an anastomosis procedure, and the region(s) of implant material 120a and/or 120b removed, thereby reestablishing a path of urine flow from the bladder (see, e.g., FIGS. 3-5).

Figure 6:
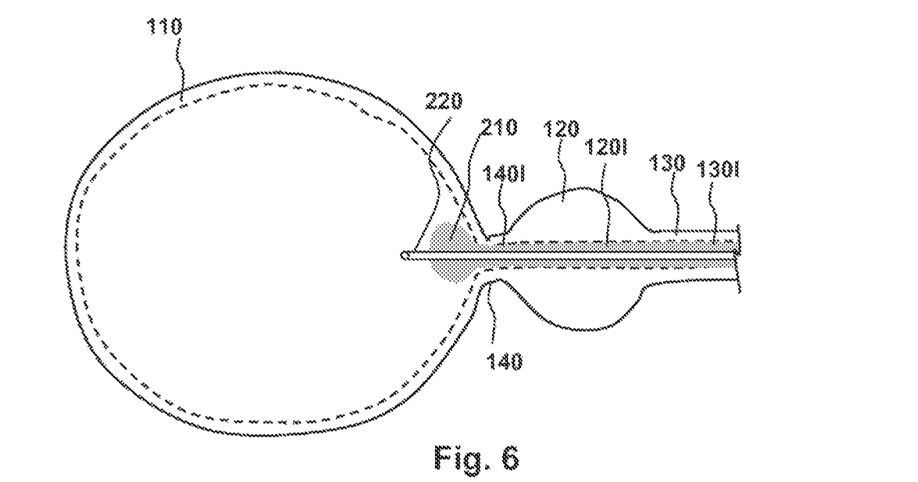
FIG. 6 is schematic illustration of a portion of the urinary tract of a male subject, after a catheter and an implant material are established within the urethra, in accordance with an embodiment of the invention.

In accordance with another embodiment of the present disclosure, as shown in FIG. 6, prior to surgical removal of the prostate 120, a catheter 220 is inserted into the urethra opening and advanced into the bladder. An implant material 210 is then established within the urethra as desired. In FIG. 6, for example, implant material 210 is present in the bladder neck lumen 1401, prostatic urethral lumen 1201 and urethral outlet lumen 1301.

Figure 7:
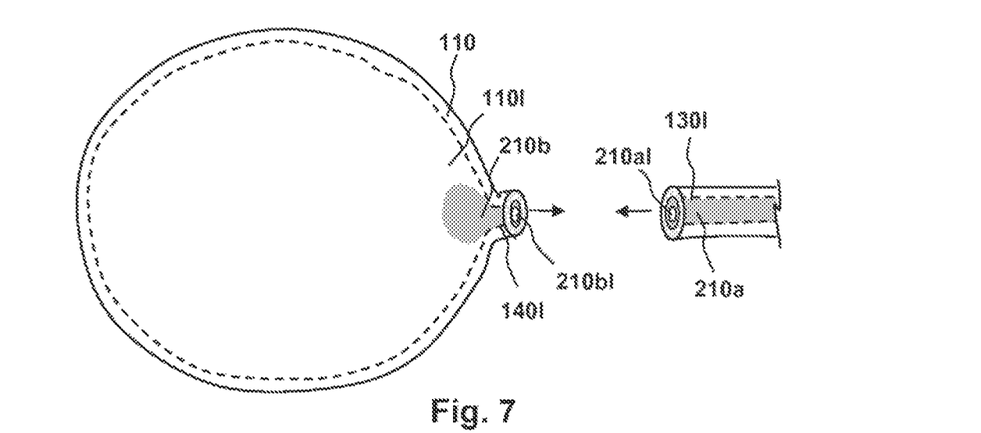
FIG. 7 is a schematic illustration of a portion of the urinary tract of a male subject as shown in FIG. 6, after removal of the prostate gland, in accordance with an embodiment of the invention.

The catheter is then withdrawn and the prostate gland surgically removed, resulting in a first region of implant material 120a being present in the urethral outlet lumen 1301 and a second region of implant material 120b being present in the bladder neck lumen 1401. Due to the withdrawal of the catheter, the first region of implant material 120a has a first lumen 120a1 and the second region of implant material 120b has a second lumen 120b1 as shown in FIG. 7. Subsequent to attachment of the bladder neck 140 to the urethral stump 130, the first and second implant materials 120a, 120b are removed, thereby reestablishing a path of urine flow from the bladder (see, e.g., FIG. 5). Because lumens 120a1, 120b1 are present in the first and second regions of implant material, 120a, 120b, respectively, urine or another removal fluid is able to readily flow through the regions of implant material 120a, 120b. This improves contact between the regions of implant material 120a, 120b and the removal fluid, thus enhancing removal of the regions of implant material 120a, 120b.

Although the catheter in FIG. 6 is removed prior to prostate resection and anastomosis, in other embodiments, the catheter remains in place during prostate resection and anastomosis, after which the catheter is withdrawn, forming lumens in the first and second regions of implant material.

Implant materials for use in the present disclosure vary widely. For example, in some embodiments, one or more regions of pre-formed solid implant material are inserted into the urethra, for example, through the lumen of a catheter or through a scope such as a cytoscope.

Examples of pre-formed solid implant materials include compressible foam materials (e.g., sponge-like materials) which are formed from water soluble materials. Examples of water soluble materials include polyvinyl alcohol, cellulose derivatives (e.g., hydroxyethyl cellulose, carhoxymethyl cellulose, etc.), polysaccharides (e.g., dextrans, starches, gums, etc.), polyethylene glycol, polyacrylamide, polyvinylpyrrolidone, polyacrylic acid and salts thereof, polymethacrylic acid and salts thereof, among many others. Such materials can ultimately be removed, for example, by natural urine flow through the urethra or by introduction of a removal fluid into the urethra (e.g., by means of a catheter) to flush the urethra.

For example, removal fluid may be fed to a catheter that has been inserted into the urethra by various means, including the use of a simple elevated container of fluid (e.g., a drip bag, etc.). In other embodiments, the removal fluid is introduced via a pump. Examples of pumps which may be employed for this purpose include positive displacement pumps such as rotary-type positive displacement pumps and reciprocating-type positive displacement pumps, for instance, rotary lobe pumps, progressing cavity pumps, rotary gear pumps, screw pumps, gear pumps, roots-type pumps, hydraulic pumps, vane pumps, regenerative (peripheral) pumps, peristaltic pumps, piston pumps, syringe pumps, and diaphragm pumps, velocity pumps, for instance, centrifugal pumps, radial flow pumps, axial flow pumps, mixed flow pumps and eductor-jet pumps, as well as buoyancy pumps, impulse pumps and gravity pumps, among others. In one specific embodiment, a vacuum-syringe-based system with check valves, such as the SAPS™—Single Action Pumping System available from Boston Scientific Corporation, Natick, Mass., USA, may be employed to pump the removal fluid.

Catheters for introduction of removal fluids into the urethra may range, for example, from 15 to 50 cm in length and from 3 to 15 French in diameter, among other possibilities.

In various other embodiments, an implant-forming composition is injected into the urethra in liquid form (e.g., using a suitable apparatus such as a catheter, scope, etc.), after which the implant-forming composition undergoes solidification, thereby establishing an implant material in the urethra. Such materials can ultimately be removed, for example, by natural urine flow through the urethra or by introduction of a removal fluid into the urethra (e.g., by means of a catheter as described above).

In one embodiment, a syringe or other pumping device (e.g., a pump selected from those listed above) may be used to inject an implant-forming composition into the body via a catheter. For example, where a syringe is employed for delivery, pressure may be applied to the syringe by hand or by an automated syringe plunger. The syringe will typically include a barrel and plunger, whereas the catheter will typically include a tube suitably constructed for insertion into the urethra and a connector for connecting the inlet port of the catheter to the syringe. The connector may be, for example a female luer fitting for engagement with a male luer fitting that is provided (e.g., attached, molded, etc.) on the syringe barrel, or may be a male luer fitting for engagement with a female luer fitting that is provided on the syringe barrel, among other possibilities.

Catheters for introduction of implant-forming compositions into the urethra may range, for example, from 15 to 50 cm in length and from 3 to 15 French in diameter, among other possibilities. Syringe barrels for introduction of implant-forming compositions into the urethra may range, for example, from 3 to 30 ml in volume, among other possibilities.

Examples of implant-forming compositions include liquids that undergo solidification as a result of physiological stimuli (e.g., a change in temperature, pH, etc.) and chemical interactions (e.g., enzymatic reactions, chemical and photo-initiated polymerization, covalent and ionic crosslinking, etc.).

In certain embodiments, an implant-forming composition may be selected that increases in viscosity, for example, exhibiting a viscosity increase of five-fold or more, ten-fold or more, twenty-fold or more, one-hundred-fold or more, or even one-thousand-fold or more, among other possibilities.

Implant-forming compositions that undergo solidification as a result of chemical interactions include those that are polymerizable into polymers in vivo. Beneficial polymers include water soluble polymers such as polyacrylic acid, polyacrylamides, polyethylene oxide and polyvinyl pyrrolidone, among others. For example, a solution containing monomers and an initiator may be injected into the urethra followed by application of electromagnetic radiation, for example, using a suitable electromagnetic-radiation-emitting catheter, resulting in polymerization. For example, the monomers may have vinyl or similar polymerizable functional groups, which can undergo photo-polymerization in the presence of a suitable photoinitiator. In some embodiments, long wavelength ultraviolet and visible wavelengths are used, as short wavelength ultraviolet is light has limited penetration depth (and may also be biologically harmful). As examples of initiators, a ketone, such as 2,2 dimethoxy-2-phenyl acetophenone may be used for ultraviolet photopolymerization, whereas camphorquinone and ethyl eosin initiators may be used for visible light polymerization, among many other possibilities. The resulting water-soluble polymer (i.e., implant material) can be subsequently removed, when desired, using a suitable removal fluid, for example, warm water, among other possibilities.

Beneficial implant-forming compositions that undergo solidification as a result of chemical interactions also include those that are ionically crosslinkable. For example, a first liquid (e.g., aqueous solution) containing an ionically crosslinkable polymer (e.g., an ionic polymer, commonly an anionic polymer) and a second liquid (e.g., aqueous solution) containing an ionic crosslinking agent (e.g., an ionic substance, commonly, a mono- or multi-valent metal cation or a cationic organic compound or polymer) may be sequentially or simultaneously (e.g., using a dual lumen catheter) injected into the urethra to create an ionically-crosslinked implant material. In certain embodiments, ionic polysaccharides such as alginates, xanthan gum, gellan gum, natural gum, agar, agarose, carrageenan, fucoidan, furcellaran, laminaran, hypnea, eucheuma, gum arabic, gum ghatti, gum karaya, gum tragacanth, locust beam gum, arabinogalactan, pectin, or amylopectin, among others, may be used as the ionically crosslinkable polymer. The resulting ionically-crosslinked implant material can be removed when desired using a suitable removal fluid, for example, water, saline or a solution that contains species that chelate crosslinking metal cations, for example, ethylene diamine tetraacetic acid, among other possibilities.

As specific examples of ionically crosslinkable polymers, k-carrageenan is known to form rigid gels upon exposure to K+ ions, whereas i-carrageenan is known to form elastic gels upon exposure to $Ca^{2+}$ ions. Gellan gum is an anionic polysaccharide that undergoes gelling in the presence of mono- and divalent cations, including $K^+$, $Na^+$, $Mg^{2+}$ and $Ca^{2+}$. Gelation of low-methoxy pectins is known to occur upon exposure to divalent cations, especially $Ca^{2+}$. In this regard, low-methoxy pectins (degree of esterification <50%) readily form gels in aqueous solution in the presence of free calcium ions, which crosslink the galacturonic acid chains. Likewise, polyguluronic acid (polyguluronate) and alginic acid (alginate) undergo gelation in presence of divalent/polyvalent cations.

Alginate is a linear copolymer with formed from β-D-mannuronate (M) residues and its C-5 epimer α-L-guluronate (G) residues, covalently linked together in different sequences or blocks. For example, the monomers can appear in homopolymeric blocks of consecutive G-residues (G-blocks), consecutive M-residues (M-blocks), alternating M and G-residues (MG-blocks), or randomly organized blocks. Alginate can be ionically crosslinked by using multivalent cations, for example, alkaline earth cations. It has been found that gel strength may decrease in the following order: $Pb^{2+}>Cu^{2+}>Ba^{2+}>Sr^{2+}>Ca^{2+}>Zn^{2+}>Co^{2+}>Ni^{2+}$, with $Sr^{2+}$, $Ba^{2+}$ and $Ca^{2+}$ are preferred in some embodiments due to their minimal toxicity. The properties of alginate will vary with the ratio of G-residues to M-residues, with lower molar ratios of M-residues to G-residues (M/G molar ratio) yielding higher hardness gels. In some embodiments, an M/G molar ratio of less than 1 is employed.

Beneficial implant-forming compositions that undergo solidification as a result of physiological stimuli include those that undergo a an increase in viscosity when warmed to body temperature (e.g., ~37° C. for humans) from a temperature below body temperature, for example, 35° C. to 30° C. to 25° C. to 20° C. to 15° C. or less, including typical room temperatures of 20° C. to 30° C. (68° F. to 86° F.). Such implant-forming compositions may also reversibly decrease in viscosity when subsequently cooled from body temperature to a temperature below body temperature (which temperature will depend on the nature of the implant-forming composition).

Thus, such implant-forming compositions may be injected into the urethra at a temperature below body temperature, after which the composition undergoes solidification due to warming in the urethra, forming an implant material in the urethra. Such implant materials can subsequently be removed from the urethra using a suitable removal fluid. For example, the urethra can be flushed with an aqueous liquid (water, saline, etc.). The removal fluid may be cooled, particularly in embodiments where the implant material reversibly decreases in viscosity when subsequently cooled from body temperature to a temperature below body temperature.

For example, in certain embodiments, a fluid implant-forming composition is injected into the body at a temperature below body temperature. As the composition equilibrates with the temperature of the body, the viscosity of the implant-forming composition increases. In preferred embodiments, an implant-forming composition may be selected that increases in viscosity (e.g., an increase of five-fold or more, ten-fold or more, twenty-fold or more, one-hundred-fold or more, or even one-thousand-fold or more, among other possibilities) as the temperature rises to the body temperature of the subject from an introduction temperature that lies in a range from 5° C. or less to 10° C. to 15° C. to 20° C. to 25° C. to 30° C. to 35° C., among other values. As a result of this increase in viscosity, an implant material is formed in the urethra.

Conversely, at a later time (e.g., after conducting an anastomosis procedure), the temperature of the implant may be reduced to below body temperature using a suitable technique, thereby rendering the implant less viscous and thus more easily removed from the body. For instance, the implant may be exposed to cold water or cold saline (e.g., using a catheter), which, in addition to reducing the viscosity of the implant, may also have the effect of dissolving the implant.

Beneficial implant-forming compositions include compositions that comprise so-called reverse thermosensitive polymers, also referred to as inverse thermosensitive polymers and reversibly gelling polymers. "Reverse thermosensitive," "inverse thermosensitive" and "reversibly gelling" refer to the property of a polymer (typically in an aqueous solution) wherein gelation (which is associated with an increase in viscosity) takes place upon an increase in temperature, rather than a decrease in temperature. "Transition temperature" refers to the temperature or temperature range at which gelation of a reverse thermosensitive polymer occurs.

Reverse thermosensitive polymers may be characterized in accordance with ASTM D-5133, which is incorporated by reference herein in its entirety. The measurements resulting from this test method are viscosity, the maximum rate of viscosity increase (the gelation index), and the temperature at which the gelation index occurs (the gelation temperature). Preferred gelation temperatures range from 30 to 37° C., among other possibilities.

Examples of reverse thermosensitive polymers include xyloglucan that is partially degraded by β-galactosidase. The sol-gel transition temperature varies with the degree of galactose elimination.

In certain other embodiments, the reverse thermosensitive polymer employed may be a block copolymer. The block copolymer may be a biodegradable, biocompatible block copolymer that comprises a polyoxyalkylene block, for example, a block copolymer comprising polyoxyethylene, blocks, polyoxypropylene blocks, or both polyoxyethylene and polyoxypropylene blocks.

In certain embodiments, the block copolymers employed have a number-average molecular weight (Mn) ranging from about 1,000 to 500,000 Daltons or more, for instance, from 1,000 to 2,000 to 5,000 to 10,000 to 20,000 to 50,000 to 100,000 to 200,000 to 500,000 Daltons or more. In certain embodiments, the polymer is in an aqueous solution. For example, aqueous solutions may contain about 5% to about 30% polymer, more typically about 10% to about 25% polymer.

The pH of reverse thermosensitive polymer solutions may vary widely, but preferably range from about 6.0 to about 7.8, which are suitable pH levels for injection into a mammalian body.

In certain embodiments, the reverse thermosensitive polymers used are poloxamers or poloxamines. Their viscosity increases and decreases with an increase and decrease in temperature, respectively. Several members of this class of polymer, including poloxamer 188, poloxamer 407, poloxamer 338, poloxamine 1107 and poloxamine 1307, show reverse thermosensitivity at or near the physiological temperature range. These polymers are members of a class that are soluble in aqueous solutions at low temperature, but which form gels at higher temperatures. For instance, poloxamer 407 is a biocompatible polyoxypropylene-polyoxyethylene block copolymer having an average molecular weight of about 12,500 and a polyoxypropylene fraction of about 30%, whereas poloxamer 188 has an average molecular weight of about 8400 and a polyoxypropylene fraction of about 20%, poloxamer 338 (Pluronic™ F108) has an average molecular weight of about 14,600 and a polyoxypropylene fraction of about 20%, poloxamine 1107 has an average molecular weight of about 14,000 and poloxamine 1307 has an average molecular weight of about 18,000.

Polyoxypropylene-polyoxyethylene block copolymers that have these properties include polymers that are available commercially as Pluronic™ poloxamers and Tetronic™ poloxamines (BASF, Ludwigshafen, Germany) and genetically known as poloxamers and poloxamines, respectively. Pluronic™ polymers have surfactant abilities and low toxicity and immunogenic responses. A specific example of such a polymer is described in Example of Pub, No. US 2008/0208163 to Wilkie, wherein LeGoo™ (poloxamer 407) at 20% aqueous concentration is used to close femoral arteries of pigs.

For further information regarding reverse thermosensitive polymers, methods of purifying the same, and methods of modifying the transition temperature of the same, among other information, see US 2008/0208163 to Wilkie.

Implant materials and implant-forming compositions in accordance with the disclosure may further include a number of supplemental agents. For example, paramagnetic or ferromagnetic materials, therapeutic agents and/or contrast-enhancing agents may be added to the compositions in some embodiments.

In this regard, as noted above, in certain embodiments, the process of drawing the bladder neck to the urethral stump may be magnetically assisted, for example, by using an implant material which is magnetic (e.g., an implant material containing magnetized materials, for instance, magnetized ferromagnetic materials such iron, nickel, cobalt, alloys of the same, etc.) or by using an implant material which is susceptible to a magnetic-field (e.g., an implant material containing ferromagnetic materials such iron, nickel, cobalt, alloys of the same, etc. and/or paramagnetic materials such as magnesium, molybdenum, lithium, tantalum, alloys of the same, etc.). In this regard, particles of magnetized or non-magnetized paramagnetic and/or ferromagnetic material may be added to the implant materials and implant-forming compositions described herein.

In certain embodiments, to aid in visualization, a contrast-enhancing agent can be added to the implant materials and implant-forming compositions described herein. Exemplarily contrast-enhancing agents are radiopaque materials, paramagnetic materials, heavy atoms, transition metals, lanthanides, actinides, dyes, and radionuclide-containing materials.

In certain embodiments, therapeutic agents, including non-steroidal anti-inflammatory agents, steroids, analgesics and antimicrobial agents, among others may be added to the implant materials and implant-forming compositions described herein.

In other aspects, the present disclosure pertains to kits which contain any combination of two or more of the following items; (a) a pre-formed implant material, (b) an insertion apparatus (e.g., a catheter and push rod) for advancing the implant material into the urinary tract of a subject, (c) a removal fluid, (d) a pump (e.g., a syringe pump) for pumping the removal fluid into the urinary tract of a subject, (e) suitable packaging material and (f) printed material (e.g., a label) with one or more of the following; (i) storage information, (ii) instructions regarding how to administer the implant material to a subject and (iii) instructions regarding how to administer the removal fluid to a subject.

In still other aspects, the disclosure pertains to kits which contain any combination of two or more of the following items; (a) an implant-forming composition, (b) an injection apparatus (e.g., a syringe and catheter) for injecting the implant-forming composition into the urinary tract of a subject, (c) a removal fluid, (d) a pump (e.g., a syringe pump) for pumping removal fluid into the urinary tract of a subject, (e) suitable packaging material and (f) printed material, (e.g., a label) with one or more of the following: (i) storage information, (ii) instructions regarding how to administer the implant-forming composition to a subject, and (iii) instructions regarding how to administer the removal fluid to the subject.

Various aspects of the invention of the invention relating to the above are enumerated in the following paragraphs:

Aspect 1. A surgical procedure for the removal of a prostate gland comprising: (a) positioning an implant material within at least a portion of the urethral outlet adjacent to the prostate, (b) removing the prostate, thereby creating a bladder neck and a urethral stump which contains the implant material, (c) securing the bladder neck to the urethral stump in an anastomosis procedure, thereby forming a shortened urethra.

Aspect 2. The surgical procedure of aspect 1, comprising positioning said implant material within the bladder neck.

Aspect 3. The surgical procedure of aspect 1, comprising positioning the implant material within the prostatic urethra and bladder neck, in addition to the portion of the urethral outlet adjacent to the prostate, whereupon the implant material is severed during removal of the prostate such that a first region of implant material is positioned within the urethral stump and a second region of implant material is positioned within the bladder neck.

Aspect 4. The surgical procedure of aspect 1, further comprising removing the implant material from the shortened urethra by flowing a removal fluid through the shortened urethra.

Aspect 5. The surgical procedure of aspect 1, wherein an implant-forming composition is injected into the urethra in liquid form and wherein the implant-forming composition solidifies to form the implant material.

Aspect 6. The surgical procedure of aspect 5, wherein a catheter is positioned in the urethra prior to injection of the implant-forming composition such that the implant material is formed around the catheter and wherein removing the catheter creates a hollow lumen in the implant material.

Aspect 7. The surgical procedure of aspect 1, wherein the implant-forming composition undergoes solidification as a result of a physiological stimulus.

Aspect 8. The surgical procedure of aspect 7, wherein the implant-forming composition undergoes solidification upon warming from an administration temperature that is lower than body temperature to body temperature.

Aspect 9. The surgical procedure of aspect 8, wherein the implant-forming composition comprises a reverse thermosensitive polymer.

Aspect 10. The surgical procedure of aspect 9, further comprising removing the implant material from the shortened urethra by flowing a chilled removal fluid through the shortened urethra.

Aspect 11. The surgical procedure of aspect 5, wherein the implant-forming composition undergoes solidification as a result of a chemical interaction.

Aspect 12. The surgical procedure of aspect 11, wherein the chemical interaction comprises ionic crosslinking.

Aspect 13. The surgical procedure of aspect 12, wherein an additional material comprising an ionic crosslinking agent is administered with the implant-forming composition.

Aspect 14. The surgical procedure of aspect 11, further comprising removing the implant material from the shortened urethra by flowing a removal fluid that comprises a chelating agent or an ion exchange agent through the shortened urethra.

Aspect 15. The surgical procedure of aspect 11, wherein the chemical interaction comprises a polymerization reaction.

Aspect 16. The surgical procedure of aspect 1, wherein the implant material is inserted into the urethra in solid form.

Aspect 17. The surgical procedure of aspect 16, wherein the implant material comprise a water-soluble polymer.

Aspect 18. The surgical procedure of aspect 16, wherein the implant material comprise a water-soluble sponge.

Aspect 19. The surgical procedure of aspect 2, wherein the implant material comprises paramagnetic or ferromagnetic particles and wherein a magnetic field assists in securing the bladder neck to the urethral stump.

Aspect 20. A medical kit comprising any combination of two or more of the following items; (a) an implant-forming composition, (b) an injection apparatus for injecting the implant-forming composition into a urinary tract of a subject (c) a removal fluid, (d) a pump for pumping removal fluid into the urinary tract, (e) suitable packaging material and (f) printed material with one or more of the following; (i) storage information, (ii) instructions regarding how to administer the implant-forming composition to the subject and (iii) instructions regarding how to administer the removal fluid to the subject.

Aspect 21. A medical kit comprising any combination of two or more of the following items; (a) a pre-formed implant material, (b) an insertion apparatus for advancing the pre-formed implant into a urinary tract of a subject, (c) a removal fluid, (d) a pump for pumping removal fluid into the urinary tract, (e) suitable packaging material and (f) printed material with one or more of the following: (i) storage information, (ii) instructions regarding how to administer the pre-formed implant material to the subject and (iii) instructions regarding how to administer the removal fluid to the subject.

Although various embodiments are specifically illustrated and described herein, it will be appreciated that modifications and variations of the present invention are covered by the above teachings and are within the purview of any appended claims without departing from the spirit and intended scope of the invention.

The invention claimed is:

1. A surgical procedure for the removal of a prostate gland comprising:
    positioning an implant material within at least a portion of the urethral outlet adjacent to the prostate;
    removing the prostate, thereby severing the implant material and creating a bladder neck and a urethral stump which contains the implant material; and
    securing the bladder neck to the urethral stump in an anastomosis procedure, thereby forming a shortened urethra.

2. The surgical procedure of claim 1, further including positioning said implant material within the bladder neck.

3. The surgical procedure of claim 2, wherein the implant material comprises paramagnetic or ferromagnetic particles and wherein a magnetic field assists in securing the bladder neck to the urethral stump.

4. The surgical procedure of claim 1, further including removing the implant material from the shortened urethra by flowing a removal fluid through the shortened urethra.

5. The surgical procedure of claim 1, further including injecting an implant-forming composition into the urethra in liquid form and solidifying the implant-forming composition to form the implant material.

6. The surgical procedure of claim 5, further including positioning a catheter in the urethra prior to injection of the implant-forming composition so as to form implant material around the catheter, and removing the catheter to form a hollow lumen in the implant material.

7. The surgical procedure of claim 5, wherein the implant-forming composition undergoes solidification as a result of a chemical interaction.

8. The surgical procedure of claim 7, wherein the chemical interaction comprises ionic crosslinking.

9. The surgical procedure of claim 8, wherein an additional material comprising an ionic crosslinking agent is administered with the implant-forming composition.

10. The surgical procedure of claim 7, further comprising removing the implant material from the shortened urethra by flowing a removal fluid that comprises a chelating agent or an ion exchange agent through the shortened urethra.

11. The surgical procedure of claim 7, wherein the chemical interaction comprises a polymerization reaction.

12. The surgical procedure of claim 1, wherein the implant-forming composition undergoes solidification as a result of a physiological stimulus.

13. The surgical procedure of claim 12, wherein the implant-form ing composition undergoes solidification upon warming from an administration temperature that is lower than body temperature to body temperature.

14. The surgical procedure of claim 13, wherein the implant-forming composition comprises a reverse thermo-sensitive polymer.

15. The surgical procedure of claim 14, further comprising removing the implant material from the shortened urethra by flowing a chilled removal fluid through the shortened urethra.

16. The surgical procedure of claim 1, wherein the implant material is inserted into the urethra in solid form.

17. The surgical procedure of claim 16, wherein the implant material comprises a water-soluble polymer.

18. The surgical procedure of claim 16, wherein the implant material comprises a water-soluble sponge.

19. A surgical procedure for the removal of a prostate gland comprising:
   positioning an implant material within at least a portion of the urethral outlet adjacent to the prostate and within the prostatic urethra and bladder neck;
   removing the prostate, thereby severing the implant material and creating a urethral stump which contains a first region of implant material and a bladder neck which contains a second region of implant material; and
   securing the bladder neck to the urethral stump in an anastomosis procedure, thereby forming a shortened urethra.

20. A surgical procedure for the removal of a prostate gland comprising:
   inserting a catheter through the urethra such that a distal end of the catheter is located within the bladder;
   injecting an implant-forming composition into the urethra and bladder in liquid form and solidifying the implant-forming composition to form the implant material;
   removing the catheter to form a lumen in the implant material;
   severing the implant material by removing the prostate thereby forming a bladder neck and a urethral stump each including an implant material portion therein; and
   securing the bladder neck to the urethral stump in an anastomosis procedure, thereby forming a shortened urethra.

* * * * *